US005618936A

United States Patent [19]
MacDonald et al.

[11] Patent Number: 5,618,936
[45] Date of Patent: Apr. 8, 1997

[54] PROCESS FOR PREPARING (S) (+)-4,4'-(1-METHYL-1,2-ETHANEDIYL)-BIS (2,6-PIPERAZINEDIONE)

[75] Inventors: Peter L. MacDonald, Arese; Riccardo Stradi, Milan; Pierluigi Rossetto, Lodi, all of Italy; Joost J. M. Holthuis, AJ Leiden, Netherlands

[73] Assignees: Sicor SpA, Italy; Chiron BV, Netherlands

[21] Appl. No.: 211,876

[22] PCT Filed: Oct. 22, 1992

[86] PCT No.: PCT/GB92/01942

§ 371 Date: Nov. 23, 1994

§ 102(e) Date: Nov. 23, 1994

[87] PCT Pub. No.: WO93/08172

PCT Pub. Date: Apr. 29, 1993

[30] Foreign Application Priority Data

Oct. 25, 1991 [GB] United Kingdom ............... 9122677

[51] Int. Cl.⁶ ............................................. C07D 241/04
[52] U.S. Cl. ..................... 544/357; 562/553; 562/554
[58] Field of Search ................ 544/357; 562/553, 562/554

[56] References Cited

U.S. PATENT DOCUMENTS 3,941,790  3/1976  Creighton ..................... 544/357
4,963,551 10/1990  Palepu et al. ................ 514/252
4,963,679 10/1990  Tu et al. ...................... 544/357
5,438,057  8/1995  Creighton ..................... 544/357

FOREIGN PATENT DOCUMENTS 0284594   9/1988  European Pat. Off. .
0409499   1/1991  European Pat. Off. .
 978724  12/1964  United Kingdom .
1234935   9/1971  United Kingdom .

OTHER PUBLICATIONS

Repta et al, *Journal of Pharmaceutical Sciences*, 65, pp. 238–242 (1976).
Wing et al, *Inorg. Chem.* 8, pp. 2303–2306 (1969).
Dwyer et al, *J. Am. Chem. Soc.* 81 pp. 2955–2957 (1959).
"Research Techniques in Organic Chemistry" by Robert B. Bates and John P. Schaefer, pp. 45–49 (1971).

*Primary Examiner*—Emily Bernhardt
*Attorney, Agent, or Firm*—Sterne, Kessler, Goldstein & Fox P.L.L.C.

[57] ABSTRACT

This invention provides a process for the preparing of (S) (+)-4,4'-(1-methyl-1,2-ethanediyl)-bis-(2,6-piperazinedione) (ICRF-187), by synthesizing a crude mixture comprising a 1,2-diaminopropane tetraacetic acid intermediate and byproducts; and then subjecting the tetraacetic acid intermediate, as part of the crude mixture, to ring formation in the presence of the byproducts, thereby producing ICRF-187 in commercially useful amounts.

17 Claims, No Drawings

PROCESS FOR PREPARING (S) (+)-4,4'-(1-METHYL-1,2-ETHANEDIYL)-BIS (2,6-PIPERAZINEDIONE)

This application is a 371 of PCT/GB92/01942 filed Oct. 22, 1992.

This invention relates to a process for preparing (S) (+)-4,4'-(1-methyl-1,2-ethanediyl)-bis(2,6-piperazinedione) (hereinafter referred to as "ICRF-187"). In particular, the invention is concerned with a practical process, utilizable on a commercial scale for the preparation of ICRF-187, in which process certain operations hitherto regarded as necessary are avoided, but which process still produces ICRF-187 of the same or better quality in very acceptable commercial yield.

ICRF-187 was described by Creighton in, inter alia, U.S. Pat. Nos. 3,941,790 and 4,275,063 as a material useful for aiding regression and palliation of cancer in mammals. In Pathologie Biologie. 1987, 35 (No 1) 49–53, Green described how certain anthracyclines are effective anti-tumour agents but carry the side effect of a tendency to produce cardiotoxicity upon chronic administration, but also disclosed for the first time that ICRF-187 could protect against such cardiotoxicity. One particular widely used anti-cancer drug suffering from the disadvantage of associated cardiotoxicity is doxorubicin hydrochloride- In U.S. Pat. No. 4,963,551, Palepu et al described a method of formulating ICRF-187 in a manner which can facilitate intravenous administration of this substance as a cardioprotective agent to reduce or prevent cardiotoxicity resulting from the administration of doxorubicin hydrochloride.

As for the manufacture of ICRF-187, Creighton, supra, essentially described two methods. In the first method, 1,2-diaminopropane tetraacetic acid is heated with formamide to result in incorporation of nitrogen and ring closure. In the second method, the tetraamide corresponding to the above tetraacid is heated in polyphosphoric acid or phenol, bringing about cyclization.

U.S. Pat. No. 4,764,614 describes an alternative synthesis in which propylenediamine tetraacetic acid tetraamide is treated in a dipolar aprotic solvent with an alkali metal derivative of dimethyl sulfoxide to form a dialkali metal salt of the desired bi-piperazinedione, the desired heterocyclic product.

EP-A-0 330 381 describe yet an alternative process or preparing, inter alia, ICRF-187, in which a corresponding tetranitrile is synthesized by reacting an appropriate diamine with formaldehyde and an alkali metal cyanide. The tetranitrile is then hydrated to yield an acid addition salt of the corresponding tetraamide, and this latter substance may then be cyclized.

These various processes for making ICRF-187 suffer from a number of disadvantage- Thus, the process of U.S. Pat. No 4764614 involves number o different chemical steps, including an esterification and amide formation. Also, the process of EP-A-0 330 381, supra, involves the use of alkali metal cyanides which are extremely toxic and consequently have substantial disadvantages in bulk handling on an industrial scale. On the other hand, the production of intermediate 1,2-diaminopropane tetraacetic acid products in other known alternative processes is generally achieved only together with the production of substantial amounts of alkali metal salt byproduct. The presence of large amounts of alkali metal salts leads to various significant processing difficulties. Furthermore, the tetraacid usually contains co-precipitated diacid and triacid impurities, the presence of which nave hitherto been regarded as prejudicial to the overall chemical efficiency and success of the process.

The problem of the presence of alkali metal salt and other byproducts has spawned significant efforts to remove such materials at the tetraacid stage, before cyclization.

Thus, in Repta et al, J. Pharmaceutical Sciences, 65(No 2) 238–242, the tetraacid product is synthesized from 1,2-diaminopropane dihydrochloride by reaction with chloroacetic acid and sodium hydroxide, and removal of salt byproduct is achieved using a cation-exchange resin column. (Glycolic acid will also De present as a by product derived from the chloroacetic acid.) This technique is very cumbersome, and quite impractical for industrial scale operation. Elution of the column requires a very substantial volume of very hot (92° C.) water, with the temperature of the column maintained at 92° C. The very significant volume of eluate is then concentrated to produce a relatively small amount (12.5 g) of the desired tetraacetic acid. Apart from being completely unsuitable on a commercial scale, this process employs a high temperature chromatography which we have now discovered leads to loss of desired product. Furthermore, the Repta et al process produces a hydrated product and not the substantially anhydrous form of starting tetraacid best suited to an efficient subsequent cyclization.

In addition, attempts at the separation of alkali metal salt and tetraacid product by fractional crystallization have resulted in significant product loss and consequent low overall yield of ICRF-187.

Moreover, using alternative precipitation techniques for tetraacid isolation, an unprocessable gel often results from precipitating tetraacid product in the presence of alkali metal salt when using an organic solvent/water mix to achieve precipitation.

This invention is based upon the discovery that, inter lia, separation of most or all alkali metal salt is, most surprisingly, unnecessary prior to cyclization; it is possible efficiently to produce a tetraacid intermediate product which can subsequently be subjected to ring formation by a method known per se thereby to produce ICRF-187 without the hitherto perceived need to remove alkali metal salt and other byproducts at the tetraacid stage. The invention enables a process In which a non-isolated tetraacid product is produced which can be dried to prepare a substantially anhydrous mixed powder (which contains byproduct in significant amounts) which can nonetheless be processed, for example, by the method of Creighton, supra, to generate the desired cyclic product, ICRF-187, in a process having as few step as reasonably possible. The overall process to ICRF-187 consequently doe not involve the use of dangerous reagents, such as alkali metal cyanides, and additionally avoids expensive and impractical separation stages such as the ion exchange chromatography process of Repta et al, supra. Furthermore, the invention is based upon the additional important discovery that deliberate co-precipitation of tetraacid product and alkali metal salt, against the prevailing prejudice, in avoiding salt separation steps used in prior art processes also avoids operations how found to be deleterious. In the overall process to ICRF-187, organic product extraction is only completely effected after the completion of cyclization.

Accordingly, the invention provides in one aspect a process for the (S) (+)-4,4$^1$-(1-methyl-1,2 ethanediol)-bis-(2,6-piperazinedione) (ICRF-187) in which an intermediate 1,2-diaminopropane tetraacetic acid product is synthesized together with byproduct salt (not necessarily, of course, sodium chloride), characterized in that the tetraacetic acid intermediate product is subjected to ring formation in the form of a crude product having substantial amounts of salt thereby to produce the desired ICRF-187.

In another aspect, the invention provides a process as above in which the tetraacetic acid intermediate product is either the free tetraacid or its disodium salt, the tetraacid intermediate product being isolated by adjusting the reaction mixture pH to about 5.3 to form the disodium salt, or to about 3 or below to form the free acid. In general, subsequent processing is substantially unimpeded whatever the pH of the reaction mixture at the stage of formation of the tetraacid, provided this pH is no higher than approximately pH 6.

In the present invention, it has now been surprisingly found that the apparently "messy" idea of co-precipitation of tetraacid intermediate and byproducts (primarily alkali metal salt), and use of the co-precipitate in a subsequent cyclization, results in a better yield than if the tetraacid is purified before cyclization. A substantially anhydrous product may be produced by adding aqueous reaction mixture containing tetraacid product, eg as obtained by following the method of Repta et al, supra [substantially the method or Wing et al, Inorg. Chem, 8,2303 (1969)], to methanol so as to result water/solvent mix in which the water generally constitutes between about 10% and about 25% (v/v) of the mix, more preferably between about 15% and about 22% (v/v), ideally about 20% (v/v). The formation of such a mix precipitates tetraacid product together with salt and other byproducts. Our experiments have shown that if the proportion of water/methanol becomes much higher than about ½ not all available tetraacid product is precipitated and losses are significant. On the other hand, if the ratio drops below about 1/10 an unprocessable gel results which cannot be used in a subsequent cyclization.

The surprising nature of these results is underlined by the fact that ocher apparently possible solvent/water systems, such as ethanol/water and acetone/water, do not work; instead of giving a clean crystalline precipitate such systems always result in an unprocessable gel which does not change to crystalline precipitate with time. We have found that dimethylformamide can be used instead of methanol, but (for economic reasons) methanol is the preferred solvent.

If the pH of the final reaction mixture prior to precipitation is such that the disodium salt is the predominant tetraacid component, the gel which first forms immediately upon precipitation in the solvent/water mixture transforms into crystals within a few minutes. If the pH is, however, lower (and the free acid is the predominant tetraacid product), the gel takes about one hour to transform into crystalline form. These are quite acceptable timings for the production of commercially usable crystalline product for subsequent cyclization.

Apart from the advantage of providing a commercially operable process for the preparation of ICRF-187, destruction of product by hydrolysis is minimized during the overall process, and the separation of ionic materials (predominantly alkali metal salt) is postponed to a point at which this separation becomes relatively easy. Thus, whereas the end product of the overall process after cyclization, ICRF-187, is covalent rather than ionic (and therefore relatively easy to separate from alkali metal salt), the intermediate tetraacid products are ionic in nature.

It will be appreciated that the process of the present invention can be applied whatever the exact synthetic route to produce the tetraacid intermediate. Furthermore, the subsequent cyclization can, if desired, follow the process described in Repta et al, supra, and U.S. Pat. No. 3,941,790.

Interestingly, if a cyclization as described in U.S. Pat. No. 3,941,790 is employed, we have also found that the need for removal of high boiling point solvent/reactant formamide can be reduced. By way of illustration, in Example 2 of U.S. Pat. No. 3,941,790 after reaction between the tetraacetic acid and formamide the resulting brown solution is evaporated under reduced pressure and the (dry) residue taken up in methanol, we have found that, in contrast, it is preferable to leave between about 100 and 200 ml of formamide for every 100 g of tetraacid product used. Thereafter, an approximately equal amount of a solvent system in which ICRF-187 is soluble but alkali metal salts are not is added to the reaction mix (still containing substantial amounts of formamide). Suitable solvents for this purpose are provided by water soluble alcohols, eg n-butanol, but dioxane or tetrahydrofuran (which simply enables the alkali metal salt to be washed away taking advantage of organic/aqueous phase separation) may also be used.

In general, ICRF-187 resulting from cyclization can be separated from the bulk of salt byproduct by, inter alia, either partition between water and a partially immiscible solvent in which ICRF-187 is soluble but not said salt or fractional crystallization with a solvent system comprising formamide and a lower alcohol.

In carrying out the overall process, initial optical resolution o the starting 1,2-diaminopropane can be conducted via the D-tartaric acid salt as described by Repta et al, supra, and this can be converted into a corresponding hydrochloride salt by treatment with hydrogen chloride in methanol, also as described by Repta et al. For ease of processing, we find that the subsequent condensation proceeds smoothly using sodium chloroacetate rather than the chloroacetic acid and sodium hydroxide as separate reagents used in the Repta et al process.

We have also found that the presence of a source of ammonia during the cyclization step of the overall process leads to a clean reaction in which organic product separation from alkali metal salt is more easily effected. The nature of the source of ammonia is not critical for this purpose, but a material such as ammonium bicarbonate is preferred because it does not introduce any other "permanent" ionic contamination into the overall reaction mixture (the bicarbonate ion readily decomposing to generate water and carbon dioxide).

After the cyclization, the product may be decolorized with charcoal if desired, and may then be crystallized from dioxane. Preferably at least three dioxane crystallizations are employed to generate a product having a purity higher than 99%. Water crystallization may be employed thereafter. The product can De used for therapeutic purposes in accordance with normal practice.

In short, the discovery of the sensitivity of the ICRF-187 to water at higher temperatures and the absence of deleterious effects from byproduct, coupled with the finding of appropriate reaction parameters, enables for the first time a process which secures the advantages of relative chemical simplicity and cheaply available starting materials (such as in the process of Repta et al. supra) whilst avoiding the impracticalities of, inter alia, the Repta et al tetraacid isolation process on m commercial scale. The belief in the art that it was necessary to separate alkali metal salt at as earlier stage as possible has been shown to be false.

The invention can thus be expressed in one respect as a process for the preparation of IRCF-187 which consists of reaction between (S)-1,2-diaminopropane and sodium chloroacetate t give (S)-1,2-diaminopropane-N,N,N',N'-tetraacetic acid which is isolated in a crude form as a co-precipitate with reaction by-products (salts) and without further purification subjected to ring formation to obtain ICRF-187.

Various aspects of the process of the present invention will become apparent from the following Examples which are given to illustrate the invention rather than limit the same. It will apparent to the skilled reader that the processing detail described in the following Examples can be modified within the scope of the present invention. The Examples in Section (A) are concerned with tetraacid production, and Section (B) deals with the subsequent cyclization. Examples (A)(1), (B)(1) and (B)(2)(g) are comparative, essentially showing the Repta/Creighton process. Example (B)(2)(h) shows what happens in the presence of increased amounts of glycolic acid, a presumed byproduct in tetraacid formation. Percentages are by weight unless otherwise specified or clear from the context.

EXAMPLES

A. PREPARING OF (S)-1,2-DIAMINOPROPANE-N,N,N$^1$, N$^1$-TETRAACETIC ACID

1. Isolation of Tetraacid with salt removal

Repta et al, supra, state that they obtained a yield, of 67% of theory, (12.5 g from 9.0 g) and since this is the best yield in a number of prior art processes, we tried to reproduce his results. Thus, chloroacetic acid (355 g, 3.75 mol) in water (200 ml) was cooled to 10° and a solution of sodium hydroxide (350 g, 8.75 mol) in water (625 ml) was added slowly so as not to exceed 20°. (S)-1,2-diaminopropane dihydrochloride (92 g, 0.625 mol ) in water (175 ml) was added and the solution allowed to stand for 7 days. The mixture was acidified with concentrated hydrochloric acid (200 ml) and concentrated to 500 ml. The resulting solids were filtered off (and found to be without optical activity, ie to not contain product), the filtrate was passed through a column of Dowex 50W-X8 cation-exchange resin (H$^+$ form, Bio-Rad Laboratories, Richmond, Calif.) and eluted with boiling water. The leavorotatory eluate was concentrated to a small volume, and the crystalline material that formed on standing was separated by filtration and dried. The yield of tetraacid was 101 g (49% of theory). Analysis of the mother liquors by optical activity showed them to contain about 5 g of product (2% of theory) (total 51%, c.f. claimed 67%).

A possible and likely explanation of this failure to match the yield claimed in the art is that some of the acid is retained by the resin. Thus, apart from the cost of the resin, its practical difficulties of high temperature requirements and its production o extremely dilute aqueous solutions, the resin step may lead to loss of product through absorption.

2. Isolation of Tetraacid without removal of substantially all salt byproduct (a) The reaction was conducted exactly as described in (1). After 7 days standing the mixture was acidified with concentrated hydrochloric acid (200 ml), which caused the temperature to rise to about 40°. This warm solution was poured quickly into methanol (10 l) at 20° to give a gel, which gradually transformed into a filtrable precipitate. The precipitate, consisting of tetraacid and salts, chiefly sodium chloride, was collected and dried at 70° under vacuum to give 309 g of tetraacid having a sodium chloride content of 42%.

(b) As in (a) above, except that he acidified reaction mixture was then concentrated under vacuum to a dense oily precipitate which upon trituration with methanol (5 l) crystallizes. The crystals, after drying under vacuum at 70°, weighed 598 g and ha a sodium chloride content of 67%.

(c) (Isolation as Disodium Salt)

The reaction was conducted as in (a) , except that the reaction mixture was acidified with concentrated hydrochloric acid (139 ml) to give pH 5.3, prior to precipitation into methanol (10 l) at 20°. The initially-formed gel transformed rapidly into a precipitate which was collected and dried at 70° under vacuum. Yield 234 g (sodium chloride conent: 13%).

(d) ( Larger Scale—With partial removal of salt by fractional crystallization)

To a mixture of (S)-1,2-diaminopropane dihydrochloride (7 kg), chloroacetic acid (27 kg) and water (30 l), contained in a 200 l glass reaction, was added at 5°–15° a solution of sodium hydroxide (26.7 kg) in water (48 l). The reaction mixture is then allowed to stand at about 20° for 7 days prior to acidification with concentrated hydrochloride acid (15.6 kg) (pH ca 3). The reaction mixture was then concentrated under vacuum to a volume of about 42 l and cooled to about 40°. The suspension was immediately filtered and the precipitate washed with cold water (2×5L) . This precipitate, which was devoid of optical activity, consisted principally of sodium chloride. The combined filtrates were diluted with methanol (130 l) at 20° and the resulting gel stirred overnight (during which time an abundant precipitate formed). The precipitate was collected using a Buchner funnel and rinsed with acetone (50 l) prior to drying at 70° under vacuum for 8 hours. Yield 19.25 kg (assay 54.5% , sodium chloride content 13.4%).

B. PREPARATION OF ICRF-187

1. Using Salt-free Tetraacid

Repta et al, Supra, obtained 46.6% yield (Creighton obtained 43% yield). We repeated this preparation, and confirmed the results as follows:

(S)-1,2-diaminopropane-N,N,N$^1$,N$^1$-tetraacetic acid (50 g) [(A)(1) above] was heated with formamide (125 ml) under nitrogen at reduced pressure at 100°–110° for 1 hour and then at 150°–155 ° for 4 hours. The brown solution was analyzed by HPLC and found to contain 35.0 g of ICRF-187. The solution was evaporated under reduced pressure at 80°–90° and the residue taken up in methanol (60 ml) anti cooled in a refrigerator overnight. Filtration, followed by washing with cold methanol and vacuum-drying gave, after re-crystallization from aqueous methanol/ether, 20 g of a white crystalline powder consisting of ICRF-187, m.p. 193° (Yield : 46% of theory).

It will be noted that 35 g of product present in the reaction mixture gives only 20 g of pure isolated product. A similar "recovery" is obtained even when salts are present in the starting tetraacid.

2. Using Salt-containing Tetraacid (a) (Salt removal from ICRF-187 by partition between tetrahydrofuran and water)

Into a suitable reactor was charged 19.25 kg of tetraacid (prepared as described in A-2.d. above, containing 54.5% of tetraacid and 13.4% of sodium chloride) and 80 l of formamide. The mixture was heated to 150°–155° and the pressure reduced to give a slow distillation. After about 5 hours the mixture contained (MPLC analysis) 7.35 kg of ICRF-187.

The brown solution was evaporated under vacuum and the residue dissolved at 50° in water (42 l) under nitrogen and extracted with tetrahydrofuran (1×75 l, 2×25 l). The combined organic extracts were treated with decolorizing charcoal, filtered through filter-aid and evaporated under vacuum. The residue was treated with methanol (17 l) and stirred overnight at 0°. The crystals were collected by filtration, rinsed with cold methanol and dried under vacuum to give 4.9 kg. A sample (49 g) was crystallized from aqueous methanol/ether giving 46.3 g of ICRF-187, mp 193°. The bulk of the product (4.85 kg) was crystallized from dioxane to give 4.58 kg of ICRF-187, mp 194°–195°.

(b) (An industrial procedure wherein salt is removed from ICRF-187 by fractional crystallization from Formamide/Methanol 1:1)

(Note that the last traces of salt are removed during dioxane recrystallization. The covalent ICRF-187 is very different in polarity, and hence solubility properties, from salt (c.f. tetraacid) and the separation is thus very easy to effect at this stage.)

Into a 50 l glass reactor was charged 10 kg of tetraacid (prepared as described in A.2.d. above, containing 54.5% of tetraacid and 13.4% of sodium chloride) and 40 l of formamide. The mixture was heated to 150°–155° and the pressure reduced to give a slow distillation (ca 5 l/hr) After 6 hours 30 l of distillate had been collected and HPLC analysis of the residue showed an ICRF-187 content of 3.82 kg. The brown solution was cooled to 50° and diluted with methanol (10 l). The temperature was brought to 50° and the abundant precipitate of odium chloride removed by filtration. The filtrate was evaporated under vacuum to oily residue, which on stirring with methanol (20 l) overnight at 0° gave a precipitate. The precipitate was collected, rinsed with cold methanol and dried under vacuum giving 2.65 kg of ICRF-187. A sample (50 g) was crytallize from aqueous methanol/ether to give 47.2 g ICRF-187, mp 193°. The remainder of the product (2.60 kg) was crystallized from dioxane to give 2.45 kg of ICRF-187, m.p. 194°–195°.

(c) (Laboratory scale procedure)

In a IL round-bottom flask was charged formamide (600 ml) and tetraacid (A.2.d) (137.5 g). These were heated under reduced pressure at 150°–155° for 4 hours, collecting 450 ml of distillate. The mixture was then cooled at 80° and diluted with 150 ml of methanol. The precipitate of salts was filtered off and rinsed with 50 ml of methanol. HPLC analysis of the filtrate showed a content of 51.4 g of ICRF-187. Isolation was as described under B.2.b. above, with final crystallization from dioxane to give pure ICRF-187 (37 g, mp 194°–195°).

(d) (Laboratory scale procedure)

As (c) but using 168 g of tetraacid prepared as in A.2.a (sodium chloride content 42%) and 600 ml formamide. HPLC analysis of filtrate showed 50.2 g ICRF-187. Isolated yield : 36 g ICRF-87, mp 194°–195° (from dioxane).

(e) (Laboratory scale procedure)

As (c) but using 325 g of tetraacid prepared as in A.2.b. and 600 ml formamide. HPLC analysis of filtrate : 51.0 g ICRF-187. Isolated yield : 36.8 g ICRF-187, mp 194°–195° (from dioxane).

(f) (Laboratory scale procedure)

As (c) but using 127 g of disodium salt of tetraacid prepared a in A.2.c. and 600 ml of formamide.

HPLC analysis of filtrate : 49.5 g TCRF-187. Isolated yield: 35.8 g ICRF-187 mp 194°–195° (from dioxane).

In illustration of yields obtainable by the present process in an overall synthesis from the starting diaminopropane dihydrochloride, the following yields can be based on certain combinations of Examples as above:

| Example | Yield (% of theory) |
| --- | --- |
| A1 and B1 (comparative) | 23.5% |
| A2a and B2d | 38.5% |
| A2b and B2e | 39.3% |
| A2c and B2f | 38.3% |
| A2d and B2b | 36.7% |

We claim:

1. A process for the preparation of (S)(+)-4,4'-(1-methyl-1,2-ethanediyl)-bis-(2,6-piperazinedione)(ICRF-187), comprising the steps of:

(a) synthesizing a crude mixture comprising a (S)-1,2-diaminopropane tetraacetic acid intermediate as a free acid or disodium salt and byproducts; and then (b) subjecting the tetraacetic acid intermediate in the crude mixture to ring formation in the presence of said byproducts, thereby producing ICRF-187 in recoverable amounts, wherein, when said ring formation is preformed using formamide, substantial amounts of formamide are not removed during ring formation.

2. A process as claimed in claim 1, wherein said tetraacetic acid intermediate is predominantly in a form selected from a free acid, a disodium salt, or a mixture thereof.

3. A process as claimed in claim 1, wherein said tetraacetic acid intermediate has been prepared by reacting (S)-1,2-diaminopropane with sodium chloroacetate or with chloroacetic acid in the presence of sodium hydroxide.

4. A process as claimed in claim 3, wherein said (S)1,2-diaminopropane has been produced as a bis-strong acid salt by treating racemic 1,2-diaminopropane with D-tartaric acid to give the diastereoisomeric bis-tartrate salt of (S)-1,2-diaminopropane followed by treating said tartrate with strong acid.

5. A process as claimed in claim 3, wherein after reaction of (S)-1,2-diaminopropane with sodium chloroacetate or with chloroacetic acid in the presence of sodium hydroxide the reaction mixture is adjusted to a pH of less than about 6.

6. A process as claimed in claim 5, wherein the reaction mixture pH adjustment is to a pH of about 5.3.

7. A process as claimed in claim 5, wherein the reaction mixture pH adjustment is to a pH of less than about 3.

8. A process as claimed in claim 1, wherein said solvent system is methanol/water or dimethylformamide/water.

9. A process as claimed in claim 8, wherein said solvent system is created by pouring an aqueous mixture containing said tetraacetic acid intermediate and said byproducts into methanol thereby to create a resulting mixture in which water is present in an amount of about 10% to about 25% (v/v) of the amount of methanol, so as to precipitate said tetraacetic acid intermediate and said byproducts as a mixture.

10. A process as claimed in claim 9, wherein said water amount is about 15% to 22% (v/v) of the amount of methanol.

11. A process as claimed in claim 9, wherein said water amount is about 20% (v/v) of the amount of methanol.

12. A process as claimed in claim 1, wherein said ring formation is effected by said tetraacetic acid intermediate and said byproducts being mixed with excess formamide and heated to produce ICRF-187.

13. A process as claimed in claim 12, wherein after said heating, formamide is removed so as to leave from about 100 ml to about 200 ml of residual formamide per 100 g of said tetraacetic acid intermediate present before said ring formation.

14. A process as claimed in claim 1, wherein ICRF-187 resulting from said ring formation is separated from the bulk of said byproducts by partition between water and a partially immiscible solvent in which ICRF-187 is soluble but not said byproducts.

15. A process as claimed in claim 14, wherein said solvent comprises one selected from a water soluble alcohol, dioxane, or tetrahydrofuran.

16. A process as claimed in claim 1, wherein ICRF-187 resulting from said ring formation is separated from the bulk of said byproducts by fractional crystallization with a solvent system comprising formamide and a lower alcohol.

17. A process as claimed in any one of claim 1, wherein salt removal from ICRF-187 resulting from said ring formation is completed by filtration of the ICRF-187 solution obtained during a crystallization from dioxane.

* * * * *